(12) United States Patent
Rondoni et al.

(10) Patent No.: US 11,324,953 B2
(45) Date of Patent: May 10, 2022

(54) PATIENT CONTROL FOR IMPLANTABLE MEDICAL DEVICE

(71) Applicant: Inspire Medical Systems, Inc., Golden Valley, MN (US)

(72) Inventors: John Rondoni, Golden Valley, MN (US); Blake D. Johnson, Golden Valley, MN (US); Quan Ni, Golden Valley, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 189 days.

(21) Appl. No.: 16/670,731

(22) Filed: Oct. 31, 2019

(65) Prior Publication Data

US 2020/0061376 A1    Feb. 27, 2020

Related U.S. Application Data

(63) Continuation of application No. 14/911,186, filed as application No. PCT/US2014/050272 on Aug. 8, 2014, now abandoned.

(60) Provisional application No. 61/864,183, filed on Aug. 9, 2013.

(51) Int. Cl.
| | |
|---|---|
| *A61N 1/372* | (2006.01) |
| *A61N 1/36* | (2006.01) |
| *A61B 5/00* | (2006.01) |

(52) U.S. Cl.
CPC .......... *A61N 1/3611* (2013.01); *A61B 5/0031* (2013.01); *A61B 5/4818* (2013.01); *A61B 5/4833* (2013.01); *A61B 5/4836* (2013.01); *A61N 1/36139* (2013.01); *A61N 1/37211* (2013.01); *A61N 1/37217* (2013.01); *A61N 1/37247* (2013.01); *A61B 5/0022* (2013.01)

(58) Field of Classification Search
CPC ................. A61N 1/37211; A61N 1/37247
See application file for complete search history.

(56) References Cited

U.S. PATENT DOCUMENTS

| | | |
|---|---|---|
| 5,172,698 A | 12/1992 | Stanko |
| D490,525 S | 5/2004 | Stein et al. |
| D544,605 S | 6/2007 | Gumisawa et al. |
| 7,505,815 B2 | 3/2009 | Lee et al. |
| D642,281 S | 7/2011 | Bachinski |
| 8,843,203 B2 | 9/2014 | Lee et al. |
| D732,673 S | 6/2015 | Lewis, Jr. et al. |
| 9,839,786 B2 | 12/2017 | Rondoni et al. |
| 2004/0230246 A1 | 11/2004 | Stein et al. |
| 2004/0268391 A1* | 12/2004 | Clercq ............ H04N 21/42204 725/37 |
| 2005/0085865 A1 | 4/2005 | Tehrani |

(Continued)

FOREIGN PATENT DOCUMENTS

| | | |
|---|---|---|
| WO | 9749454 | 12/1997 |
| WO | 2010059839 | 5/2010 |

OTHER PUBLICATIONS

International Search Report and Written Opinion dated Jun. 27, 2016 from PCT Application No. PCT/US2016/026954,12 pages.

(Continued)

*Primary Examiner* — George R Evanisko
(74) *Attorney, Agent, or Firm* — Dicke, Billig & Czaja, PLLC (57) ABSTRACT

A patient control is disclosed that facilitates operation of an implantable medical device.

17 Claims, 6 Drawing Sheets

(56) References Cited

U.S. PATENT DOCUMENTS

| | | |
|---|---|---|
| 2005/0115561 A1 | 6/2005 | Stahmann et al. |
| 2006/0190047 A1 | 8/2006 | Gerber et al. |
| 2007/0270921 A1* | 11/2007 | Strother ............ A61N 1/37211 607/60 |
| 2008/0221644 A1 | 9/2008 | Vallapureddy et al. |
| 2008/0249591 A1 | 10/2008 | Gaw et al. |
| 2009/0287103 A1 | 11/2009 | Pillai |
| 2010/0064212 A1 | 3/2010 | Snyder |
| 2010/0137938 A1 | 6/2010 | Kishawi et al. |
| 2010/0222845 A1 | 9/2010 | Goetz |
| 2010/0305663 A1* | 12/2010 | Aghassian ......... A61N 1/37247 607/61 |
| 2010/0318159 A1* | 12/2010 | Aghassian ......... A61N 1/37229 607/59 |
| 2010/0318519 A1 | 12/2010 | Hadjieleftheriou et al. |
| 2011/0172744 A1 | 7/2011 | Davis et al. |
| 2011/0264164 A1 | 10/2011 | Christopherson et al. |
| 2012/0101551 A1 | 4/2012 | Aghassian et al. |
| 2012/0215285 A1 | 8/2012 | Tahmasian et al. |
| 2013/0104314 A1 | 8/2013 | Miller, III et al. |
| 2013/0197607 A1 | 8/2013 | Wilder et al. |
| 2013/0268026 A1 | 10/2013 | Rao et al. |
| 2014/0067005 A1 | 3/2014 | Kaula et al. |
| 2014/0074180 A1 | 3/2014 | Heldman et al. |
| 2014/0277248 A1 | 9/2014 | Younker et al. |
| 2015/0367136 A1 | 12/2015 | Rondoni et al. |
| 2016/0193468 A1 | 7/2016 | Rondoni et al. |
| 2016/0303388 A1 | 10/2016 | Rondoni et al. |

OTHER PUBLICATIONS

JP Office Action Summary for 2016-533457, filed Feb. 9, 2016.
2009 Bionic Navigator Software Guide.
Search Report, International Searching Authority, PCT, Mar. 4, 2015, 7 pages.

* cited by examiner

PATIENT CONTROL FOR IMPLANTABLE MEDICAL DEVICE

CROSS-REFERENCE TO RELATED APPLICATIONS

This application is a Continuation Application of U.S. patent application Ser. No. 14/911,186, filed Feb. 9, 2016, which is a U.S. National Stage Patent Application of PCT/US2014/050272, filed Aug. 8, 2014, and which claims the benefit of U.S. Provisional Patent Application No. 61/864,183, filed Aug. 9, 2013, incorporated by reference herein.

BACKGROUND

A targeted electrical stimulation of a nerve shows great promise in a number of therapies. In one example, such stimulation is implemented via an implantable medical device, such as but not limited to, an implantable pulse generator.

BRIEF DESCRIPTION OF THE DRAWINGS

The accompanying drawings are included to provide a further understanding of examples and are incorporated in and constitute a part of this specification. The drawings illustrate examples and together with the description serve to explain principles of examples. Other examples and many of the intended advantages of examples will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific examples in which the invention may be practiced. In this regard, directional terminology, such as "top," "bottom," "front," "back," "leading," "trailing," etc., is used with reference to the orientation of the Figure(s) being described. Because components of examples can be positioned in a number of different orientations, the directional terminology is used for purposes of illustration and is in no way limiting. It is to be understood that other examples may be utilized and structural or logical changes may be made without departing from the scope of the present disclosure. The following detailed description, therefore, is not to be taken in a limiting sense.

At least some examples of the present disclosure are directed to a patient remote control for an implantable medical device and/or a related patient management system. In some examples, the patient remote control forms part of an at least partially implantable nerve stimulation system for treating obstructive sleep apnea. However, it will be understood that the patient remote control and/or patient management system are applicable to implantable medical devices other than for treating obstructive sleep apnea. In some examples, such other implementations include therapies, such as but not limited to, central sleep apnea, complex sleep apnea, cardiac disorders, and respiratory disorders.

These examples, and other examples, are further described in association with at least FIGS. 1-7.

Figure 1:
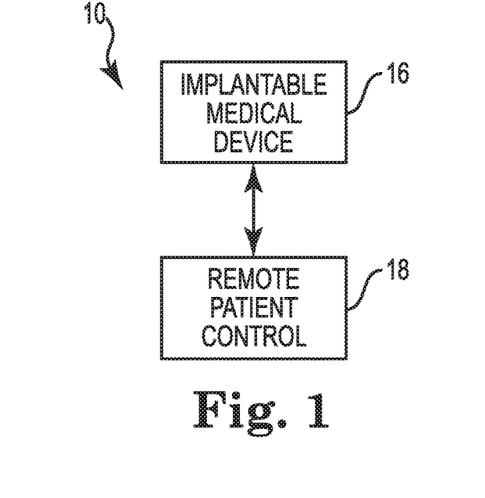
FIG. 1 is a block diagram schematically illustrating a treatment system, according to one example of the present disclosure.

FIG. 1 is a block diagram schematically illustrating a treatment system 10, according to one example of the present disclosure. As shown in FIG. 1, treatment system 10 includes an implantable medical device 16 and a patient remote control 18 in selective communication with the implantable medical device 16. In some examples, the implantable medical device 16 performs diagnostic and/or therapeutic functions in a patient's body while the patient remote control 18 controls at least some functions of the implantable medical device 16. Other functions are pre-programmed into the implantable medical device 16 and/or controllable via a separate care/physician controller (not shown). In some examples, patient remote control 18 includes at least some of substantially the same features and attributes as the patient remote control 200, 250 (FIGS. 3A-3D, 4A-4E, 5), with or without at least some of the features of a patient management system like that described in association with FIGS. 6A, 6B, 7.

Figure 2:
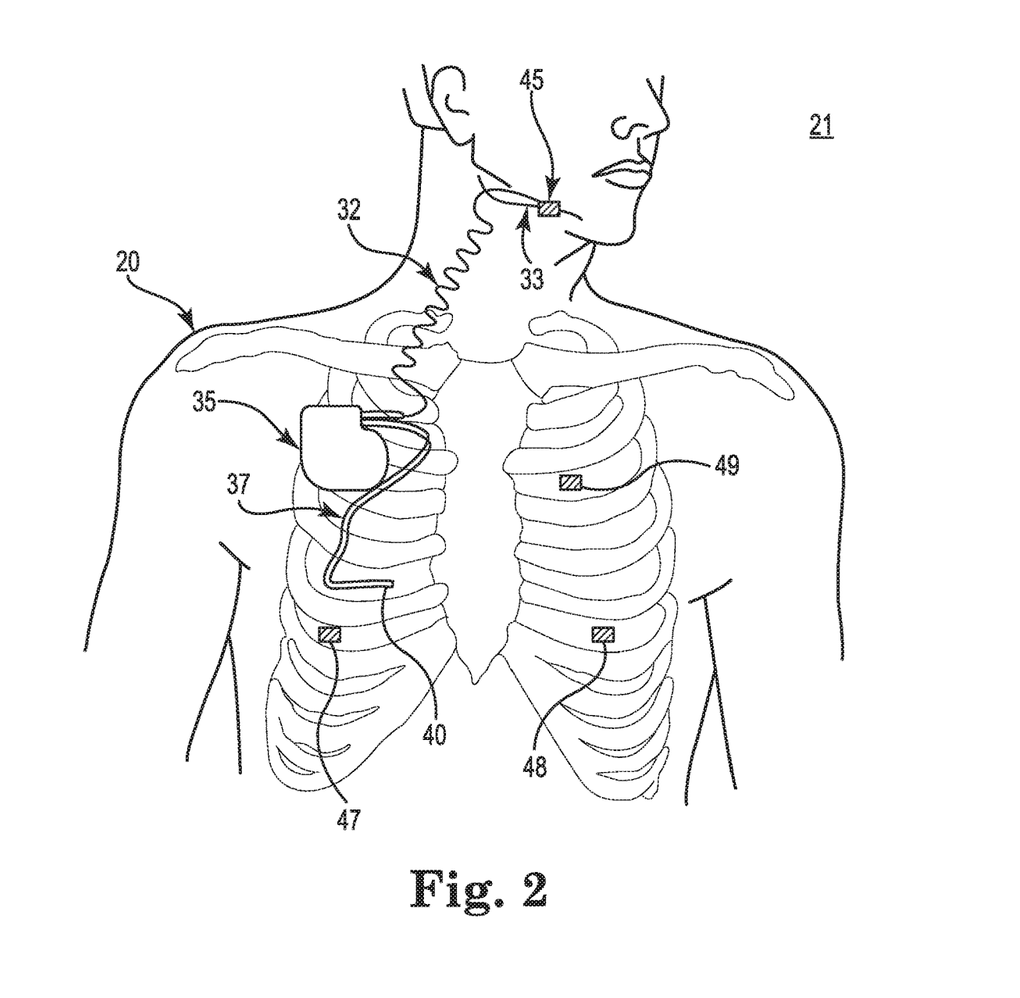
FIG. 2 is a diagram schematically illustrating an at least partially implantable stimulation system relative to a patient, according to an example of the present disclosure.

While system 10 is applicable to many different types of implantable medical devices, in one example the implantable medical device 16 comprises an implantable pulse generator of a system to treat obstructive sleep apnea via nerve stimulation. Accordingly, FIG. 2 schematically illustrates an at least partially implantable stimulation system, according to an example of the present disclosure. As illustrated in FIG. 2, in some examples system 21 includes an implantable pulse generator (IPG) 35 and a stimulation lead 32 electrically coupled with the IPG 35 via a connector (not shown) positioned within a connection port of the IPG 35. In some examples, the IPG 35 is surgically positioned within a pectoral region of a patient 20. The lead 32 includes a stimulation electrode portion 45 and extends from the IPG 35 so that the stimulation electrode portion 45 is positioned in contact with a desired nerve, such as the hypoglossal nerve 33 of the patient 20, to enable stimulation of the nerve 33, as described below in detail. In some examples, the stimulation electrode portion 45 comprises a self-sizing cuff such as described in U.S. Pat. No. 8,340,785 to Bonde et al. In some examples, lead 32 includes features and attributes at least consistent for use in an implantable stimulation system as described in U.S. Pat. No. 6,572,543 to Christopherson et al., and which is incorporated herein by reference in its entirety.

In some examples, the system 21 comprises an additional lead 37 including at least one sensor portion 40 (electrically coupled to the IPG 35 and extending from the IPG 35) positioned in the patient 20 for sensing respiratory effort. The sensor portion 40 detects respiratory effort including respiratory patterns (e.g., inspiration, expiration, respiratory pause, etc.) in order to trigger activation of an electrode portion to stimulate a target nerve. Accordingly, with this arrangement, the IPG 35 (FIG. 1) receives sensor waveforms from the respiratory sensor portion 40, thereby enabling the IPG 35 to deliver electrical stimulation synchronously with inspiration (or synchronized relative to another aspect of the respiratory cycle) according to a therapeutic treatment regimen in accordance with examples of the present disclosure. It is also understood that the respiratory sensor portion 40 is powered by the IPG 35 and the IPG 35 also contains internal circuitry to accept and process the signal from the lead 37.

In some examples, the sensor portion 40 is a pressure sensor. In one example, the pressure sensor in this example detects pressure in the thorax of the patient. In some examples, the sensed pressure could be a combination of thoracic pressure and cardiac pressure (e.g., blood flow).

In some examples, the respiratory sensor portion 40 comprises a bio-impedance sensor or pair of bio-impedance sensors and can be located in regions other than the pectoral region. In one aspect, such an impedance sensor is configured to sense a bio-impedance signal or pattern whereby the control unit evaluates respiratory patterns within the bio-impedance signal. For bio-impedance sensing, in one example, electric current will be injected through an electrode portion within the body and an electrically conductive portion of a case of the IPG 35 (FIG. 3A) with the voltage being sensed between two spaced apart electrode portions (or also between one of the electrode portions and the electrically conductive portion of the case of IPG 35) to compute the impedance.

In some examples, system 21 also comprises additional sensors to further obtain physiologic data associated with respiratory functions. For example, system 21 may include various sensors (e.g., sensors 47, 48, 49 in FIG. 1) distributed about the chest area for measuring a trans-thoracic bio-impedance signal, an electrocardiogram (ECG) signal, or other respiratory-associated signals.

In some examples, system 21 includes other internal or external sensors such as blood oxygenation sensors and/or acoustic sensors, for detecting snoring, cardiac activity, respiratory airflow, etc. In some examples, such sensors include sensors for detecting body activity, body position/posture, etc. In some examples, various combinations of physiologic sensors are employed.

In some examples, the sensing and stimulation system 21 for treating obstructive sleep apnea is a totally implantable system which provides therapeutic solutions for patients diagnosed with obstructive sleep apnea. However, in some examples, one or more components of the system are not implanted in a body of the patient. A few non-limiting examples of such non-implanted components include external sensors (respiration, impedance, etc.), an external processing unit, or an external power source. Of course, it is further understood that the implanted portion(s) of the system provides a communication pathway to enable transmission of data and/or controls signals both to and from the implanted portions of the system relative to the external portions of the system. The communication pathway includes a radiofrequency (RF) telemetry link or other wireless communication protocols.

Whether partially implantable or totally implantable, the system is designed to stimulate the hypoglossal nerve during some portion of the repeating respiratory cycle to thereby prevent obstructions or occlusions in the upper airway during sleep.

Figure 3A:
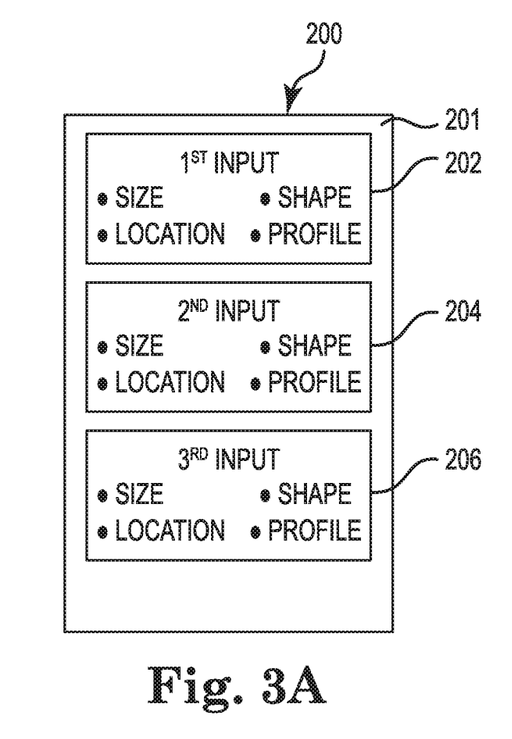
FIG. 3A is a block diagram schematically illustrating an input portion of a patent remote control, according to one example of the present disclosure.

FIG. 3A is a block diagram schematically illustrating a patient remote control 200, according to one example of the present disclosure. In some examples, patient remote control 200 includes at least some of substantially the same features and attributes of patient remote control 18, as previously described in association with at least FIG. 1.

As shown in FIG. 3A, in some examples the patient remote control 200 includes a first input 202, a second input 204, and a third input 206. In some examples, each of the first, second, and third inputs 202, 204, 206 have a unique size, shape, location, and topographical profile that differs from the other respective inputs. With this arrangement, a patient can quickly and effectively distinguish between the three different inputs using tactile senses (e.g. touching) and/or visual sensing. Use of tactile sense to distinguish between the three different inputs increases the usability of the system when it is used in the sleep environment which is often dark or dimly lit. Further examples of these characteristics of the first, second, third inputs are described later in association with at least FIGS. 4A-4B.

Each of the first, second, and third inputs 202, 204, 206 is assigned a particular function or functions arranged in a complementary manner. In some examples, one of the respective inputs can implement an "on" function, while another respective input can implement an "off" function, and the remaining respective input can implement an increase/decrease function. In some examples, at least one of the inputs 202, 204, 206 is a physical button activatable via finger pressure. In some examples, at least one of the inputs is a touch-screen type button, which generally does not move under finger (or stylus) pressure but which is nonetheless activatable via finger contact and/or finger pressure.

Figure 3B:
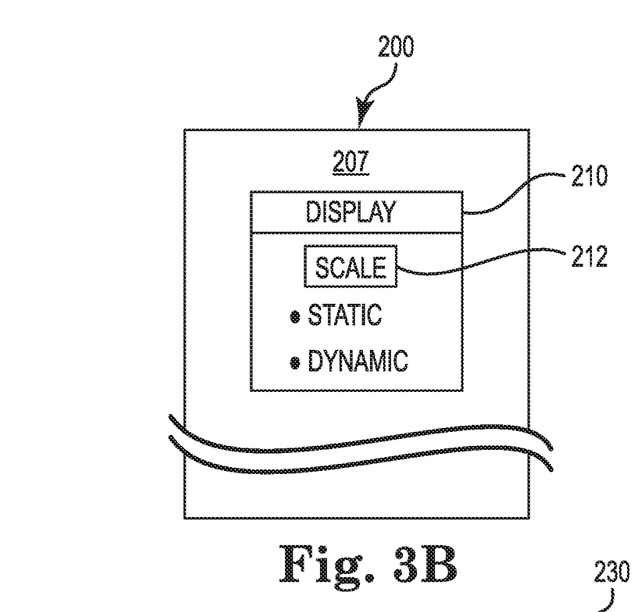
FIG. 3B is a block diagram schematically illustrating an output portion of a patent remote control, according to one example of the present disclosure.
Figure 3C:
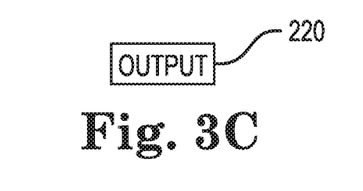
FIG. 3C is a block diagram schematically illustrating an output portion of a patent remote control, according to one example of the present disclosure.

In addition, in some examples, a first side 201 of patient remote control 200 includes at least one output 210, as shown in FIG. 3C. In some examples, output 210 includes an indication an "on" or "off" status of the patient control 210 while in some examples, output 210 indicates other a status of other functions. In one aspect, output 210 is implemented via one element or multiple elements. In some examples, output 210 is implemented as a light provided via a LED or other light source. In some examples, output 210 is co-located with or closely adjacent one of the first, second, or third inputs 202, 204, 206.

In some examples, a second side 207 (e.g. a back side) of patient remote control 200 includes a display 210, which in general terms, provides for display of information relating to at least some of the functions of first, second, and third inputs 202, 204, 206. In one aspect, the display 210 includes static components, such as a light that is in either an on state or an off state, and/or dynamic components, such as a blinking light.

Figure 3D:
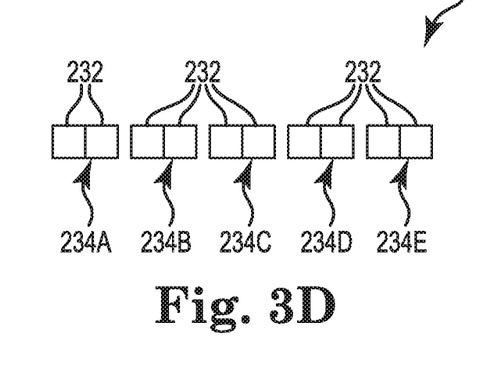
FIG. 3D is a block diagram schematically illustrating an output portion of a patent remote control, according to one example of the present disclosure.

In some examples, display 210 includes a scale function 212 for indicating a scale of input values. In some examples, scale function 212 is implemented via an array 230 of light indicators 232, as shown in FIG. 3D. In one aspect, the light indicators 232 are arranged in pairs 234A, 234B, 234C, 234D, 234E. In some examples, each light indicator 232 is made of a light emitting diode (LED). At least one implementation of the scale function 212 via array 230 of indicators 232 is further described later in association with at least FIG. 3D.

Figure 4A:
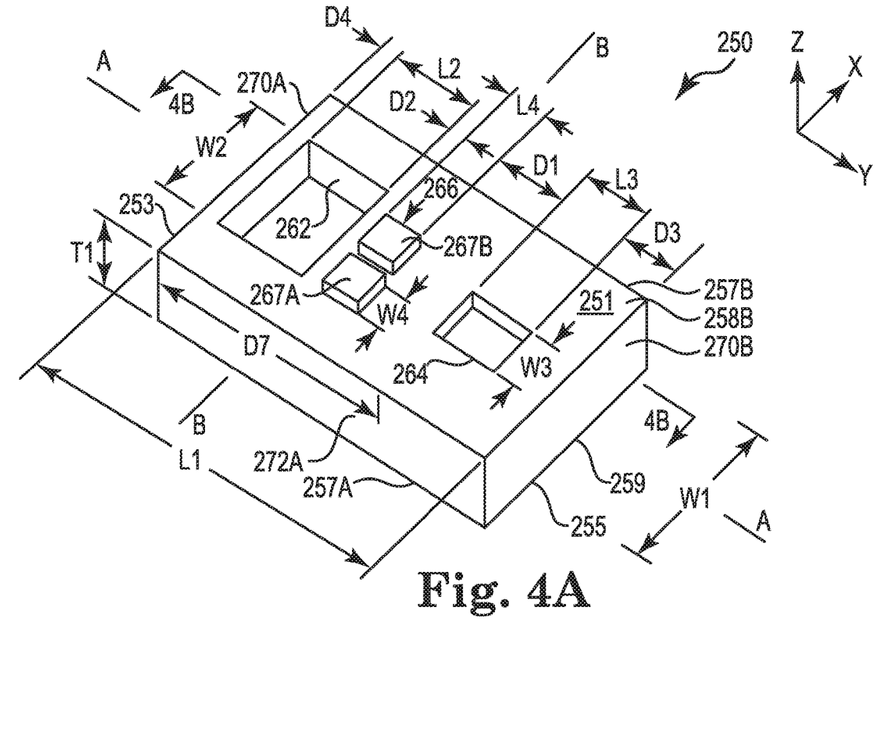
FIG. 4A is a diagram including a perspective view schematically illustrating a patient control, according to one example of the present disclosure.
Figure 4B:
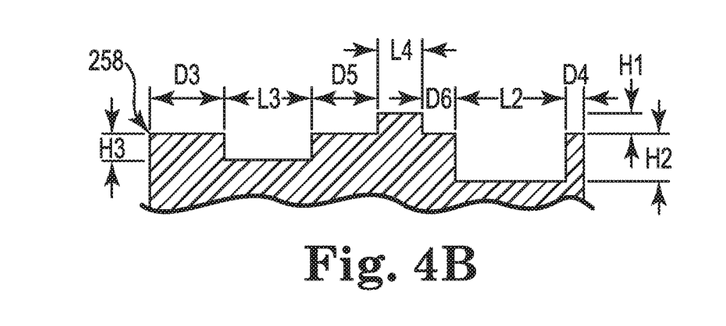
FIG. 4B is a sectional view as taken along lines 4B-4B in FIG. 4A, according to one example of the present disclosure.

FIG. 4A is a perspective view of a patient remote control 250, according to one example of the present disclosure, which provides one example implementation of the patient remote control 200 of FIGS. 3A-3C. FIG. 4B is a partial sectional side view of patient remote control 250 of FIG. 4A.

As shown in FIG. 4A, patient remote control 250 includes a housing 251 having a first end 253 and opposite second end 255, as well as opposite sides 257A, 257B, a top surface 258 and opposite, back surface 259. In some examples, housing 251 further includes opposite end portions 270A, 270B and opposite side portions 272A, with housing 251 having a thickness (T1), length (L1), and width (W1).

As further shown in FIG. 4A, patient remote control 250 includes a first input 262, second input 264, and third input 266. In some examples, first input 262 and second input 264 are each arranged as a recessed activatable button, which can either be implemented as a button defining a recess or as a generally flat button movable within a separate recess defined in top portion 258 of housing 251 of the patient remote control 250. In some examples, third input 266 is interposed between the first and second inputs 262, 264 and in some examples, is raised from top surface 258 of housing 251, as shown in FIG. 4A. While FIG. 4A shows third input 266 as multiple elements 267A, 267B, in some examples third input 266 comprises a single element.

In some examples, at least one of the first, second, third inputs is located on a face or portion (e.g. 270A, 270B, 272A, 272B) other than top surface 258 of housing 251.

In some examples, first input 262 comprises an "on" button for placing the patient control in an "on" state, which includes automatic transmission of a request to the implantable medical device (e.g. 16 in FIG. 1) to start therapy. In some examples, first input 262 also functions as a "pause" button, the pressing of which pauses an active therapy and re-pressing causes resumption of active therapy.

In some examples, second input 264 comprises an "off" button for transmitting a request to the implantable medical device to terminate a therapy session.

In some examples, third input 266 comprises an increase portion 267A and decrease portion 267B, which enable a patient to increase or decrease an intensity of therapy, respectively, and which includes transmits a request to the implantable medical device (e.g. 16 in FIG. 1) to increase or decrease the intensity of therapy, respectively.

As shown in FIGS. 4A-4B, the third input 266 is interposed between the longitudinally spaced apart, respective first and second inputs 262, 264, with third input 266 being raised from top surface 258 of housing 251. In one aspect, this arrangement separates the first "on/pause" input 262 and the second "off" input 264 into separate and distinct locations on the housing 251, thereby inhibiting accidental or inadvertent engagement of the first and second inputs 262, 264.

Moreover, as further show in FIGS. 4A-4B, first input 262 is spaced apart from first end 253 by a relatively short distance D4, while second input 264 is spaced apart from first end 253 by a relatively long distance D7. Accordingly, a user will be able to immediately differentiate the identity of the two respective inputs 262, 264 based on their relative locations on top surface 258 of housing 251. Moreover, second input 264 is spaced apart from second end 255 by a distance D3, which is a multiple (3×, 4×, 5×) of the distance D4, to further facilitate the user differentiating an identity of the second input 264 relative to first input 262, which is much closer to its adjacent first end 253.

In some examples, as further shown in FIG. 4B, first input 262 has a different topographical aspect, i.e. depth (H2) which is substantially greater (e.g. 2×, 3×, 4×) a depth (H3) of second input 264, further differentiating an identity of the respective inputs 262, 264 relative to each other. Moreover, with both first and second inputs 262, 264 being recessed relative to top surface 258 of housing 251, these inputs have topographical aspects which are significantly different than the topographical aspect of third input 266, which is raised from the top surface 258 of housing 251 by a height (H1) and interposed between the respective recessed inputs 262, 264.

In some examples, all of the first, second, and third inputs 262, 264, 266 are aligned along a single elongate orientation (represented by y) which is centered on the housing 251 along the lateral axis/orientation (represented by x). However, in some examples, at least one of the respective inputs 262, 264, 266 has an "off-axis" location that is closer to one of the first side 272A or the second side 272B of housing. This arrangement further differentiates an identity of such input because of its non-aligned position relative to the other inputs. In one example, second input 264 has an off axis location in which second input is closer to one of the respective opposite sides 272A, 272B.

In some examples, second input 264 has a different size and/or shape than first input 262. In one example, as shown in FIG. 4A, second input 264 occupies a differently sized area than first input 262 and presents a more elongated rectangular shape, which is oriented generally to parallel a longitudinal axis A of housing 251. In this way, an identity of the second input 264 is further differentiated from the identity of the first input 262. In one aspect, the area of first input 262 is characterized by its length L2 and width W2 while the area of second input 264 is characterized by its length L3 and width W3. While FIG. 4A depicts first input 262 as having a substantially larger area than second input, in some examples, second input 264 has a substantially larger area than first input 262. In either case, these distinctions further contribute to the tactile signature or identity of each of the respective inputs.

Figure 4C:
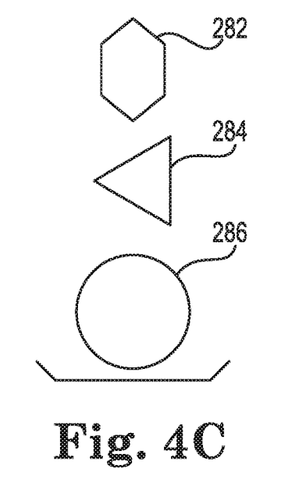
FIG. 4C is a diagram schematically illustrating an array of shapes for an input of a patient remote control, according to one example of the present disclosure.

It will be understood, of course, that the first, second and third inputs, 262, 264, 266 are not limited to rectangular shapes, and can exhibit other shapes/orientations, such as but not limited to an polygon shape 282, triangular shape 284, and circular shape 286, as illustrated in FIG. 4C. Accordingly, in some examples, upon providing at least one of the inputs 262, 264, 266 with one of these non-rectangular shapes, the identities of the respective inputs 262, 264, 266 are further differentiated for tactile and visual senses of the user.

Figure 4D:
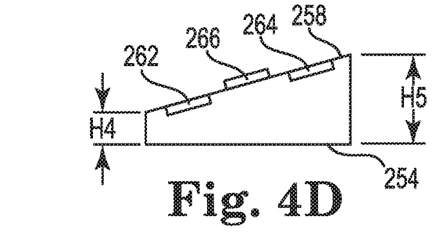
FIG. 4D is a side view schematically illustrating a profile of a patient remote control, according to one example of the present disclosure.

In some examples, as seen in the side profile view of FIG. 4D, the patient remote control 250 includes a housing 251 that has generally flat bottom surface 259 and a generally sloped or tapered top surface 258, such that one of the respective inputs (e.g. first input 262) will have a relatively small height near first end 253 (having a height H4) and one of the other respective inputs (e.g. second input 264) will have a relatively large height near second end 255 (having a height H5). This arrangement further differentiates the identity (via tactile and visual senses) of the respective inputs 262, 264 while simultaneously inducing a proper orientation of the patient's hand relative to the housing 251 such that the first input 262 will naturally become oriented adjacent the fingertips of the patient.

In one aspect, when any number of these multiple features is combined together, the identities of the first input 262, second input 264, and third input 266 are quickly and effectively distinguished from one another by the tactile senses and/or visual senses. Consequently, the presentation of first input 262 of having a different size, shape, topographical profile, and relative location on housing 251 as compared to second input 264 (and third input 244) significantly enhances user operation of patient remote control 250 in low-lighting settings and/or by those with vision impairments.

Some later described examples provide for a user operation in which one of the inputs (e.g. 262, 264, 266 in FIG. 4A) is activated via a finger press and then the patient remote control 250 is moved over an implanted medical device (e.g. 16 in FIG. 1, 35 in FIG. 2) to allow transmission of the activated request. However, by strategically differentiating an identity of the first, second, third inputs (according to at least the examples associated with FIGS. 4A-4C), one mode of user operation includes placing the patient remote control 250 on the body over the implanted medical device, and then activating a desired function via a finger press of one of the inputs (e.g. 262, 264, 266) such that the patient remote control 250 is already positioned for transmission of the request to the implanted medical device. In particular, with the first input 262 having a unique location (first end 253 of housing 251), unique depth (deeper recess), unique elevation (due to sloped profile of top surface 258 of housing 251), unique size/shape, etc., a user can use a single hand and fingertips to readily orient the patient remote control 250 on the body (e.g. pectoral region) without having direct sight of the top surface 258 of the housing and is still able to confidently engage a respective first, second, and third input as desired. As previously noted, in some examples, the patient remote control 250 employs audible signals to confirm activation of one of the inputs and/or confirms transmission of a request via an activated input such that the user can hear confirmation of a deployed function while still holding the patient remote control 250 over their body near the implanted medical device. In combination, these features significantly enhance operation of the patient remote control 250 in low-lighting settings and/or for those with visual impairments.

In one example, when patients awake during sleep they will typically want to pause therapy for a period until they have fallen back asleep. With that in mind, when the first input 262 embodies an "on/pause" function, the first input 262 provides a large, deeply recessed, and centrally located target so that right or left-handed patients can quickly and immediately locate the pause button embodied in first input 262.

In contrast, when the second input 264 is embodied as an "off" button, its location away from the first input 262 (and third input 266) and its recessed profile helps a patient avoid accidentally engaging the off button during the night. Moreover, when one does desire to engage the "off" button, the relative smaller size of the second input 264 also aids in a quick identification of the "off" button relative to the on/pause button. In some examples, the area of the "off" button (e.g. in this example, second input 264) is generally equal to or smaller than an area of a thumb print of the patient, further immediately indicating to the use that their thumb or finger is placed over the second input 264 because of the sharp contrast in size (as well as depth of recess, location, shape, etc.) relative to the first input 262, such some examples in which the first input 262 is larger than a size of a patient's thumb print.

Meanwhile, in some examples, the third input 266 includes two elements 267A, 267B which embody an increase and decrease function, respectively. As previously noted, the third input 266 has a raised profile relative to top surface 258 of housing 251 (and raised relative to the recessed first input 262). In one aspect, this raised profile prevents accidental activation when patients intend to press the on/pause button (i.e. first input 262) and/or facilitate identification of third input 266. Moreover, when the third input 266 is embodied as two separate adjacent elements 267A, 267B (instead of a single element), the user is able to further differentiate the third input 266 from the first and second inputs 262, 264, which are each embodied in a single button configuration. In some examples, the third input 266 includes a surface coating and/or material different than the material/coating used for the first input 266 buttons to further differentiate the third input 266 from the first input 262.

Figure 4E:
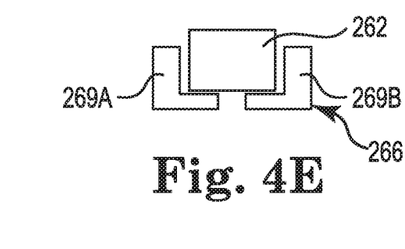
FIG. 4E is a diagram including a top view schematically illustrating an input of a patient remote control, according to one example of the present disclosure.

In some examples, as shown in FIG. 4E, the third input 266 is implemented as two separate elements 269A, 269B, which are shaped and arranged to at least partially surround the first input 262, which aids the patient in discerning the identity/location of the first input 262. While the separate elements 269A, 269B in FIG. 4E have a generally L-shaped configuration, it will be understood that such elements can have other shapes suitable to fully or partially surround a periphery of first input 262. Moreover, in some examples, the third input 266 is implemented in more than two separate elements, which together partially surround or fully surround the periphery of the first input 262.

In some examples, the housing 251 includes a light color to enhance visibility of the device in a dark room.

In some examples, the third input 266 enables a patient to adjust the strength of therapy, at least within a pre-set range set by a physician, set as a factory default, and/or automatically determined via a protocol of a patient management system. Moreover, in some examples, the third input 266 enables the patient to provide input to an automatic titration protocol.

In one aspect, the pre-set range of selectable strengths is a therapeutic range, in which the selectable strengths provide an acceptable therapy response. In general terms, when such therapy involves nerve stimulation (such as for treating obstructive sleep apnea) patients will decrease stimulation strength to enhance comfort and patients will increase stimulation strength to increase therapy effectiveness such as if they notice snoring or increased daytime sleepiness. In some examples, control of stimulation strength includes control of stimulation parameters such as voltage, current, pulse width, rate, and the stimulation electrode configuration. In some examples, one of the elements 267A of the third input 266 of patient remote control 250 corresponds to an increase button while the other element 267B corresponds to a decrease button.

In some examples, the display 210 of a patient remote control (200 in FIGS. 2A-3B, 250 in FIGS. 4A-4B) informs a patient how many stimulation steps they have available to them and, where the currently selected stimulation strength is relative to a maximum or minimum value. In particular, as shown in FIG. 3B, display 210 includes a scale component 212 by which indications of stimulation strength are automatically scaled based on the range of values available to the patient. For example, as previously noted in association with FIG. 3D, one such scaled display 210 comprises a linear array 230 of indicators 232 arranged in 5 groups of 2 LEDs, to provide a total of ten light indicators. Accordingly, if the patient has 5 stimulation strength settings available, then the LEDs will reflect (via being lit or unlit) an increase and decrease in groups of 2. However, in examples in which the patient has 10 stimulation strength settings available, then the LEDs (via being lit or unlit) will increase and decrease one at a time. In another example, if the patient had 3 stimulation strength settings, then the LEDs will illuminate 3 or 4 at a time.

Moreover, the display 210 is configured such that each control step is reflected via blinking at an appropriate LED following an amplitude increase or decrease. If an increase is requested, then the LED associated with a new amplitude step would blink and then become solid. Conversely, if a decrease is requested, then the LED associated with the new amplitude step would blink and then turn off. In this way, the patient will understand the size and direction of each control step.

In one aspect, examples in which display 210 is implemented via array(s) of LEDs tend to generate less electrical noise than screen-type displays, which makes an LED-based display 210 more conducive for use in sensitive applications such as low power and inductive telemetry communications with implantable medical devices, like IPG 35 in FIG. 2. Moreover, employing LED arrays in display 210 provides for superior longevity and ruggedness as compared to screen-type displays, which typically have shorter life cycles, use more battery power, and are more susceptible to breakage, such as if a patient control were dropped, stepped on, etc.

In some examples, patient remote control (200 in FIGS. 3A-3C; 250 in FIGS. 4A-4C) includes output 220 (FIG. 3C) on a first side 201 on which the respective inputs 262, 264, 266 are located. In general terms, output 220 indicates a status of operation of an implanted medical device (e.g. implantable pulse generator) associated with patient remote control 250. In some examples, output 220 is a light-based indicator, which can be lit, unlit, or operate in a blinking mode. In some examples, when lit or flashing, the output 220 displays different colors to indicate different states of operations of the remote patient control and/or implanted medical device. For example, one color (e.g. green) can be used to indicate that therapy is "on" or "paused", while another color (e.g., yellow or red) can be used to indicate that the therapy is "off." Meanwhile, in some examples, in combination with one of the respective different colors, flashing of the output 220 is used to differentiate on/off and/or on/pause.

In one aspect, output 220 overcomes several challenges that might otherwise be faced by a patient. First, because telemetry communications with an implanted device are often short range, in order to transmit a command from the patient remote control to the implanted device (e.g. implantable pulse generator), the patient remote control is placed on the body directly over a location of the implanted device. However, in the case of traditional button/controller configurations, this placement on the body typically makes it difficult for the patient to confirm which buttons of a patient remote control are being pressed because they cannot see which buttons are being pressed. However, by providing a visual indication via output 220 in examples of the present disclosure, a patient is informed with confirmations of which buttons were pressed and/or the state of operation of the patient control. Moreover, when output 220 is combined with the unique configuration of first, second, and third inputs 262, 264, 266 (as described in some examples of the present disclosure), which provide tactile and visual cues regarding the identities of the respective inputs, a patient becomes well-equipped to discern the operation of the patient control before and after manipulation of the inputs 262, 264, 266 of the patient control.

Moreover, in some examples, the patient control is designed so that when patients turn therapy "on", therapy (e.g. nerve stimulation) does not immediately begin. Instead therapy is delayed for a period of time and/or until the IPG detects sleep and/or obstructive respiratory events. In some instances, a short burst of therapy (e.g. nerve stimulation) is applied to notify the patient that therapy has been turned "on", but that burst can be missed by the patient. In other instances, when a patient turns off their therapy or pauses their therapy, they can feel that therapy has stopped, but it may not be clear to the patient if therapy is paused or off.

In any of these situations, the output 220 provides information to the patient regarding the state of operation of the implanted medical device (e.g. implantable pulse generator).

In some examples, a display indicator of output 220 is also designed to produce a low-level light that would not be disturbing when in a dark room, but would be sufficient to provide ambient feedback as to the therapy status when not directly observed. For instance, the display indicator of output 220 would illuminate the subject's hand (and some surrounding space) when the patient holds the device. Moreover, upon placement of the patient remote control on a nightstand, the output 220 would cause a lampshade or wall to similarly illuminated until the indicator of output 220 times out. In some examples, the light intensity is selected to provide feedback in a dark or dimly lit sleep environment; in other examples the light intensity is automatically adjusted based on the ambient light levels such that higher intensity light is used in a more brightly lit room and a lower intensity light is used in a more dimly lit room.

In some examples, output 220 is co-located with first input 262 on top surface 258 of housing 251. In one aspect, this location increases the ease of the patient seeing the illumination from output 220 when the patient remote control 250 is placed over the body for communication with the implanted medical device. In some examples, output 220 is located elsewhere on housing 220. It will be understand that output 220 is not limited in its shape and/or size, except for being complementary with a shape/size/location of other inputs 262, 264, 266 on housing 251. In some examples, output 220 at least partially surrounds the first input 262 and may be juxtaposed in close proximity to portions of the third input 266. By doing so, the illumination from output 220 helps to highlight the location of the first input 262 (e.g. on/pause function), which facilitates initiating or pausing therapy in a low-lighting environment.

In some examples, patient remote control 250 further includes auxiliary alerts (e.g. tones or vibration) to supplement the manner/type of information communication via the display indicator of output 220. In some examples, such alerts are produced in association with at least some functions of a communications module, such as but not limited to, communications module 400 as further described later in association with at least FIG. 5.

In general terms, patient remote control 250 exchanges information with an implantable device (IMD) 16 regarding basic functions such as therapy intensity (e.g. stimulation strength), on/off/pause, etc. However, in some examples the patient remote control 250 also obtains information regarding various IMD settings and data such as, but not limited to, therapeutic intensity range, serial number, and date of last configuration by a physician. Because these values do not change quickly they do not need to be updated each time the patient remote control 250 communicates with the IMD 16. In one aspect, this information provides a foundation from which accurate feedback may be provided to the patient regarding stimulation strength and more effective therapy metrics, such as but not limited to, the therapy protocol further described later in association with at least FIG. 7.

As previously noted, because communications to/from an implantable medical device 16 often involve short-range communications due to low power constraints, operation of such communications (e.g. telemetry link) between the patient remote control 250 and the implantable medical device 16 is generally limited to a small window of relative positions/spacing.

Figure 5:
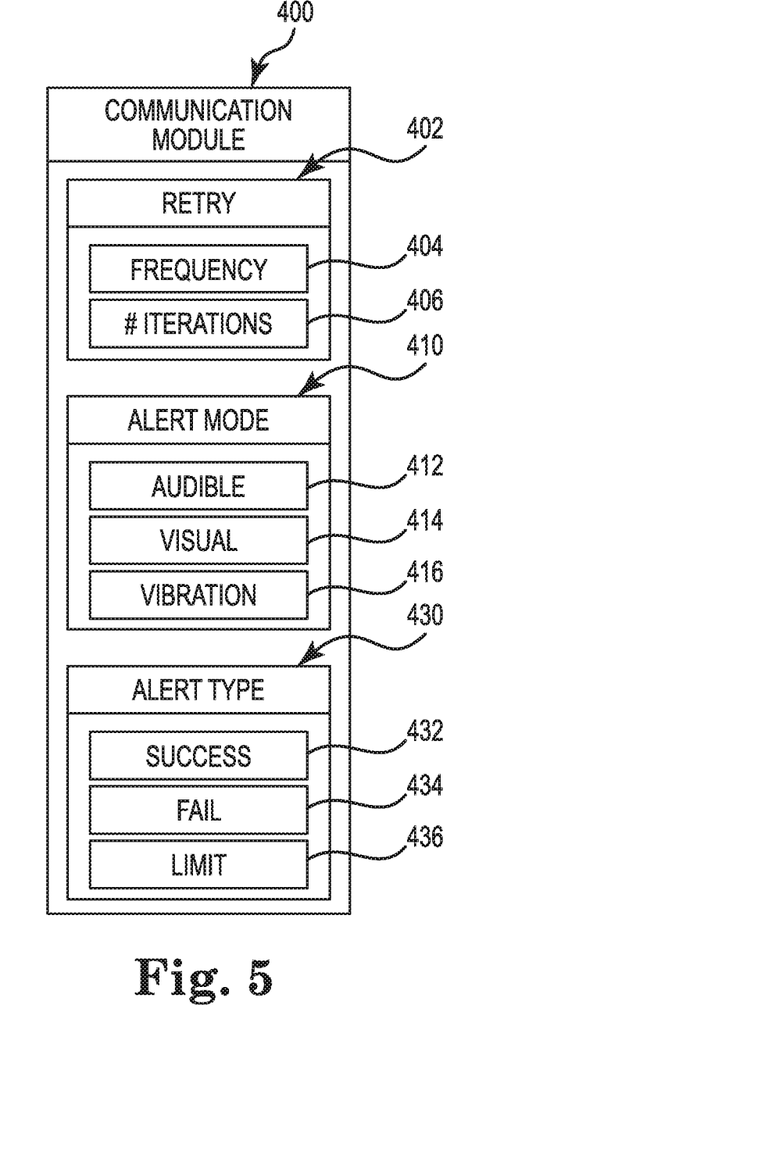
FIG. 5 is a block diagram schematically illustrating a communications module, according to one example of the present disclosure.

With this in mind, some examples of the present disclosure provide a patient remote control having a communications module tailored to this situation. FIG. 5 is a block diagram schematically illustrating one such communications module 400 of a patient remote control 18, 250, according to one example of the present disclosure.

As shown in FIG. 5, among other basic features typical of a patient remote control, communications module 400 includes a retry function 402.

In some examples, the retry function 402 operates in cooperation with an alert mode array 410 and/or alert type array 430. It will be understood that in some examples, the alert mode array 410 and/or alert type array 430 support other functions of communications module 400 and/or other functions of the patient remote control 250, such as providing notifications associated with basic operation of the inputs 262, 264, 266 relative to an implantable medical device. It will be understood that in at least some examples, the notifications illustrated in association FIG. 5 are not communicated as "alerts" such that no imminent action or negative consequence is necessarily associated with the occurrence of the notification.

In some examples, the retry function 402 of the patient remote control 250 automatically retransmits (e.g. retries) a communication to an implantable medical device, such as a command until a confirmation is successfully retrieved from the implantable medical device, at which point the patient remote control 250 provides a notification to the patient. In some examples, such notifications are provided via one of audible indicator function 412 (e.g. tones, beeps, etc.), visual indicator function 414 (e.g. lights), and vibration indicator function 416 of alert mode array 410, or via a combination of these modalities.

In some examples, each notification falls into one of several classes. As shown in FIG. 5, the alert type array 430 provides a success indicator function 432 and a failure indicator function 434 by which the communications module 400 communicates to the patient a successful implementation of a command by the implantable medical device and a failed implementation of a command by the implantable medical device, respectively. In addition, limit indicator function 436 communicates to the patient that a requested command was not implemented because of an existing limit for the particular command requested. For example, if the patient pressed the third input 266 in an attempt to increase therapy intensity (e.g. stimulation strength) but the requested amount exceeds a limit set by the physician, then the limit indicator function 436 provides a notification to the patient of the existence of the limit.

In providing the different types of alerts (e.g. success, failure, limit), any one of the different modes (e.g. audible, visual, vibration) of notification can be employed, as well as various combinations of more than one mode.

With this arrangement provided via communications module 400, the patient remote control 250 enables a patient to select a command and then wave the patient remote control 250 over the location of the body hosting the implanted medical device instead of the patient using an alternate technique of holding the patient remote control 250 over the location of body hosting the implanted medical device while selecting a command via the patient remote control 250. This arrangement makes communications with the implanted medical device easier for the patient, and also allows the patient to periodically manipulate the patient remote control 250 into a position more favorable to look at output 220 or display 210 of patient remote control 250 regarding an indication of the operational state of the implanted medical device.

In some examples, the retry function 402 is configured to send a command as an absolute command (as opposed to a relative command) to ensure that certain types of commands (e.g. an increase therapy intensity command) are not successively sent upon each retry. Otherwise, the therapy intensity could be increased far beyond the requested level of increase (but still subject to a safety limit). However, in some examples, the retry function 220 permits multiple retries or transmissions of a single "on" or of a single "off", because multiple retries will merely result in multiple executions by the implantable medical device of the same command, without a change in the ultimate action taken by the implantable medical device. In some examples, the patient remote control 250 is equipped to set a therapy intensity (e.g. stimulation strength) at a particular numerical level via the patient remote control 250 in cooperation with a display device 540, as further described later in association with at least FIG. 6A.

In some examples, the patient remote control 250 allows a patient to use third input 266 to scroll through options in a relative range of provided therapy intensity adjustments and once the patient achieves the desired level displayed (e.g. via display 210 in FIG. 3B, 3D), the patient waves the patient remote control 250 over the implanted medical device. In one aspect, the automatic retry function 240 implements an absolute level command that corresponds to the level of therapy intensity displayed in display 210 that was just selected, and then changes the target level as the patient continues to toggle through the options.

As noted above, in at least some instances, in addition to sending commands to the implantable medical device, the patient remote control 250 retrieves data from the implanted medical device. In some examples, such data retrieval is performed to provide accurate feedback and metrics to the patient, with such feedback/metrics being viewable via a display device 540 coupled to the patient remote control 250, as further described later in association with at least FIG. 6A and with such feedback/metrics employed in a therapy protocol (FIG. 7), in some examples.

Figures 6A, 6B:
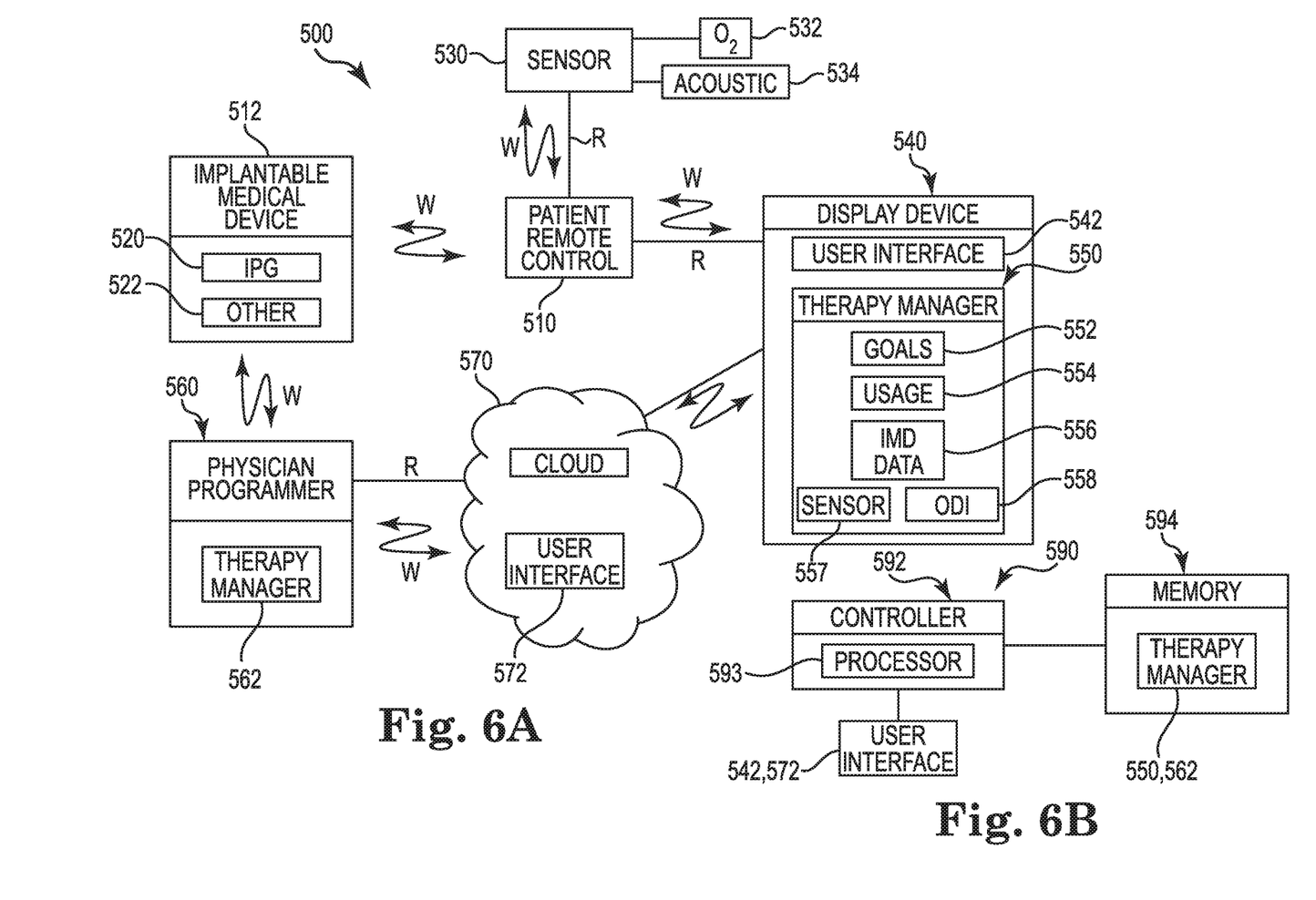
FIG. 6A is a block diagram of a patient management system, according to one example of the present disclosure.
FIG. 6B is a block diagram of a control portion, according to one example of the present disclosure.

With this in mind, the patient remote control 250 forms part of a larger patient management system 400, as shown in FIG. 6A in which a display device 540 (e.g. smartphone, tablet, computer, etc.) is in communication with the patient remote control 250, as further described below.

FIG. 6A is a block diagram schematically illustrating a patient management system 500, according to one example of the present disclosure.

Among other components, the patient management system 550 includes a patient remote control 510 having at least some of substantially the same features and attributes as patient remote control 250 as previously described in association with at least FIGS. 4A-5, and includes an implantable medical device 512 having at least some of substantially the same features and attributes as implantable medical device 16, as previously described in association with at least FIG. 1 and throughout the present disclosure.

As shown in FIG. 6A, the patient remote control 510 is in selective wireless communication with the implantable medical device 512 to send/receive commands/data when the patient remote control 510 is placed in sufficiently close proximity to the implantable medical device (IMD) 510. In some examples, the patient remote control 250 retrieves data from IMD 510 on a periodic basis (instead of continuously) to prevent unnecessary delay in more primary communications between the patient remote control 250 and IMD 510. In some examples, the patient remote control 250 is configured to retrieve data from the IMD 510, such as when therapy is turned off. By collecting the IMD data at such opportunities, the patient remote control 250 can retrieve data from the IMD 510 about therapy performance over the last night as well as a new therapy range that might have been selected by an IMD titration protocol during the previous night.

In some examples, the patient remote control 250 retrieves data from the IMD 510 when the patient remote control 250 attempts to select an absolute amplitude value that the IMD 510 rejects as out of the therapy range. In this scenario, the IMD 510 returns information to the patient remote control 250 indicating an acceptable amplitude value or indicating that the requested amplitude value is too high. In some examples, such notifications are provided via the limit function 436 of alert type array 430 of communications module 400 of FIG. 5.

In one illustration of the preceding scenario, when the command requested via input 266 to set a new therapy level as an absolute amplitude value fails, the patient remote control 510 determines that the information stored in the patient remote control 510 regarding the therapy range is out of date and retrieves more current data from the implantable medical device 512. This current data now stored in the patient remote control 510 includes upper and lower allowable therapy intensity limits, such that when the patient attempts such increases and decreases in therapy levels via third input 266, patient remote control 510 sends absolute commands instead of relative increment and decrement commands. For example, supposing the patient remote control 510 retrieved the updated range from the implantable medical device 512, with the range being 2.1 to 2.4 and the current amplitude at 2.2. When the patient pushes the increase button of third input 266, the patient remote control will send the 2.3 command (an absolute amplitude value) to the implantable medical device 512 instead of a relative increment command.

In some examples, implantable medical device 512 comprises an implantable pulse generator for treating obstructive sleep apnea (520) via nerve stimulation, but in some examples, the implantable medical device 510 is configured for other therapeutic modalities (522).

In addition, as further shown in FIG. 6A, in some examples the patient management system 500 includes an external sensor 530, such as but not limited to, an external oxygen saturation sensor 532 and/or acoustic sensor 534, both of which are available in the sleep environment of the patient.

In one aspect, external sensor 530 provides objective feedback to the implantable medical device 510 and/or other components (e.g. a therapy manager) of the patient management system 500 to facilitate providing efficacious therapy. In some examples, the sensor 530 communicates wirelessly (as represented via W) or via a wired connection (as represented via R) such as via USB modalities. Wireless communication includes, but is not limited to, various wireless communication protocols such as Bluetooth, Near Field Communication (NFC), etc.

In some examples, patient remote control 510 is in selective communication with a display device 540 via a wireless (W) or wired (R) connection, as shown in FIG. 6A. In one aspect, such wireless communication includes additional more powerful wireless modalities, such as WIFI, GSM, etc. In some examples, display device 540 includes a user interface 542 and a therapy manager 550. Some familiar examples of suitable display devices include a mobile/smart phone, tablet, notebook computer, desktop computer, etc.

In some examples, display device 540 includes user interface 542, such as but not limited to, a graphical user interface for enabling inputs (e.g. keyboard, stylus) and display of information, thereby providing for access to and operation of therapy manager 550.

In general terms, display device 540 hosts a therapy manager 550 to provide a tool by which a patient can become informed about details of their therapy provided via the implanted medical device 512 and related functioning of the patient remote control 510. In one aspect, the therapy manager 550 is accessible via user interface 542. Accordingly, among other potential features, in some examples, therapy manager 550 includes a goals function 552, a usage function 554, and an IMD data function 556.

In general terms, the goals function 552 tracks and communicates therapy goals to the patient. In some examples, as further described later in association with at least FIG. 7, the goals function 552 also communicates positive reinforcement regarding success in meeting goals and/or encouragement for improvement on unmet goals. In some examples, such goal-related information is communicated via email status updates, private tweets, SMS messaging (e.g. text messaging), game-like interfaces, trends, graphs, reports, and recorded or live messages from care providers/managers (e.g. clinician, nurse, physician etc.)

In some examples, usage function 554 communicates details regarding times of use, duration of use each day, number of days used within a week, etc. regarding the manner of use of the therapy system by the patient.

In some instances, the patient remote control 510 captures data directly from on operation of the inputs 262, 264, 266 of the patient remote control (e.g. 250 in FIG. 4A-4B). For example, such data might include therapy usage time, based on when the therapy is turned on and turned off via inputs 262, 264, as well as pause times and the times of the day in which the therapy is utilized. In some instances, the usage function 554 tracks adjustments in therapy intensity, such as implemented via third input 266 of patient remote control 250, 510.

In some examples, the therapy manager 550 includes an IMD data function 556 to communicate information tracked and stored by the IMD 510. In examples in which the IMD 510 is adapted for treating obstructive sleep apnea, such data might be tracked via usage function 554 and include information regarding a tracked apnea-hypopnea index (AHI), sleep quality, such as a frequency, volume, intensity of awakenings, etc. This information is conveyed to the display device 540 via the patient remote control 510.

For instance, the therapy history parameter reports trends in the frequency, volume, stimulation strength of stimulation over one or more periods of time (e.g. day, week, month, etc.). Other potentially data reportable via the therapy history parameter includes trends in the frequency, volume, intensity etc. of awakenings and apnea-hypopnea index (AHI). In some examples, via a separate programmer 560, a physician or care manager determines which type and volume of information is available to the patient.

Via the user interface 542, these metrics are displayed in a positive and engaging manner that recognizes the positive aspects of the patient behavior, trends use/strength/behavior over time, and provides goals and recommendations for how the patient can improve their sleep quality and/or therapeutic outcome, as further described later in association with at least FIG. 7.

Providing such therapy information via a user interface 542, the patient management system 500 increases the likelihood of patient engagement in therapy, which in turn, promotes positive impressions of the therapy and likewise can improve therapy adherence. Therapy adherence is directly related to the effectiveness of the therapy. Lack of patient adherence is a recognized problem with other sleep therapies such as CPAP and mandibular advancement.

In some examples, the therapy information provided via the therapy manager 550 of display device 540 is communicated to a physician programmer 560 via the cloud 570 (e.g. internet-based communication network) or even directly via short-range wireless (W) communication or wired (R) communication when the physician programmer 560 happens to be co-located with the display device 540. As shown in FIG. 6A, the physician programmer 560 includes a therapy manager 562 which includes at least some features in common with the therapy manager 550 of display device 540, thereby enabling the physician (or other care manager) to manage the care of the patient. Upon receiving such patient information at programmer 560, the physician performs actions like setting goals for the patient viewable in the patient user interface 542, sending messages to the patient to encourage or praise the patient, and/or determining a need for a patient office visit to address any use or performance issues. In some examples, the patient management system 500 includes a web-based portal (e.g. user interface 572) to perform such analysis and/or communications.

In some examples, in addition to guiding a patient toward successful engaging their therapy, therapy manager 550, 562 is configured to automatically titrate the IMD therapy settings based on IMD data 556 and the patient's use of the patient remote control 510, with such adjusted or titrated settings being communicated to the IMD 512 and/or even patient remote control 510. In one aspect, the user interface 542 does not necessarily communicate to the patient all of the more technical aspects of the therapy. With this arrangement, a patient's improved engagement of implanted treatment system is coupled with an automatic titration of the therapy parameters.

In some examples, a therapy manager (e.g. 550, 562) is stored in a memory of the display device 540, physician programmer 560, cloud computing resource 570, etc. In some examples, a therapy manager including all or part of the functions and features of therapy manager 550 is stored in a memory of patient remote control 510. Regardless of the location of the therapy manager (or portions thereof), in some examples, the therapy manager forms part of and/or is supported by a control portion 590, which is further described below in association with at least FIG. 6B. The control portion 590 can be housed in whole, or in part, in display device 540, physician programmer 560, cloud computing resource 570, and/or patient remote control 510.

With this in mind, in some examples a patient remote control for an implantable medical device comprises a therapy manager to at least partially manage a therapy applied via the implantable medical device, wherein the therapy manager includes a blood oxygenation sensor function 557 as shown in FIG. 6A to track and store patient blood oxygenation data, such as obtained via a blood oxygen sensor 532 (e.g. pulse oximeter) worn by the patient. As in other examples, the patient remote control includes at least first and second inputs to activate and terminate therapy, as well as at least some of the other inputs/functions consistent with the examples of a patient remote control in the present disclosure. In some examples, this therapy manager also includes a usage function to track and store information on patient use of the patient remote control to implement therapy via the implantable medical device.

In this example, the patient remote control forms part of a system further comprising a pulse oximeter (represented by oxygen sensor 532) selectively couplable to the patient remote control 510 to provide the patient blood oxygenation data to the blood oxygenation sensor function 557 in FIG. 6A. In some examples, the therapy manager is configured to automatically modify a therapy parameter, or automatically provide indications to modify a therapy parameter, based on at least the patient blood oxygenation data (per sensor function 557). In some examples, the therapy parameter includes at least one of a stimulation amplitude, a stimulation pulse width, a stimulation rate, a stimulation duty cycle, a patient control amplitude limit, a patient control pulse width limit, a stimulation limit, and a patient control rate limit.

In some examples, the therapy manager is configured to calculate an oxygen desaturation index (as represented via ODI 558) in FIG. 6A based on the patient blood oxygenation data. In some examples, the therapy manager is configured to automatically modify a therapy parameter, or automatically provide indications to modify the therapy parameter, if the oxygen desaturation index (ODI 558) exceeds a threshold. In some examples, the therapy manager is configured to automatically modify a therapy parameter, or automatically provide indications to modify the therapy parameter, if the oxygen desaturation index (ODI 558) falls below a threshold.

In some examples, the therapy manager is configured to communicate to a cloud computing resource 570 at least one of the patient blood oxygenation data, the therapy parameter, or a modification to the therapy parameter for storage and access by at least one of a clinician (e.g. physician, care manager, etc.) and a patient.

FIG. 6B is a block diagram schematically illustrating one control portion 590, according to one example of the present disclosure. In some examples, control portion 590 includes a controller 592, a memory 594, and a user interface 542/572.

In general terms, controller 592 of control portion 590 comprises at least one processor 593 and associated memories that are in communication with memory 594 to generate control signals directing operation of at least some components of the systems and components described throughout the present disclosure. In some examples, these generated control signals include, but are not limited to, operation of therapy managers 550/562, user interface 542, 572 and the various components, modules, etc. of the patient management system 500. In some examples, a control portion 590 (or portions thereof) is present in implantable medical device 512 and/or patient remote control 510.

In particular, in response to or based upon commands received via a user interface 542/572 and/or machine readable instructions (including software), controller 592 generates control signals in accordance with at least some of the previously described examples and/or later described examples of the present disclosure. In some examples, controller 592 is embodied in a general purpose computer while in other examples, controller 592 is embodied in the various ion writing assemblies described throughout the present disclosure.

For purposes of this application, in reference to the controller 592, the term "processor" shall mean a presently developed or future developed processor (or processing resources) that executes sequences of machine readable instructions (such as but not limited to software) contained in a memory. In some examples, execution of the sequences of machine readable instructions, such as those provided via memory 594 of control portion 590 cause the processor to perform actions, such as operating controller 592 to perform imaging while preventing corrosion as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium, as represented by memory 594. In some examples, memory 594 comprises a computer readable tangible medium providing non-volatile storage of the machine readable instructions executable by a process of controller 592. In other examples, hard wired circuitry may be used in place of or in combination with machine readable instructions (including software) to implement the functions described. For example, controller 592 may be embodied as part of at least one application-specific integrated circuit (ASIC). In at least some examples, the controller 592 is not limited to any specific combination of hardware circuitry and machine readable instructions (including software), nor limited to any particular source for the machine readable instructions executed by the controller 592.

In some examples, user interface 542/572 comprises a user interface or other display that provides for the simultaneous display, activation, and/or operation of at least some of the various components, functions, features, and of control portion 590 and/or therapy managers, as described throughout the present disclosure. In some examples, at least some portions or aspects of the user interface 542/572 are provided via a graphical user interface (GUI).

Figure 7:
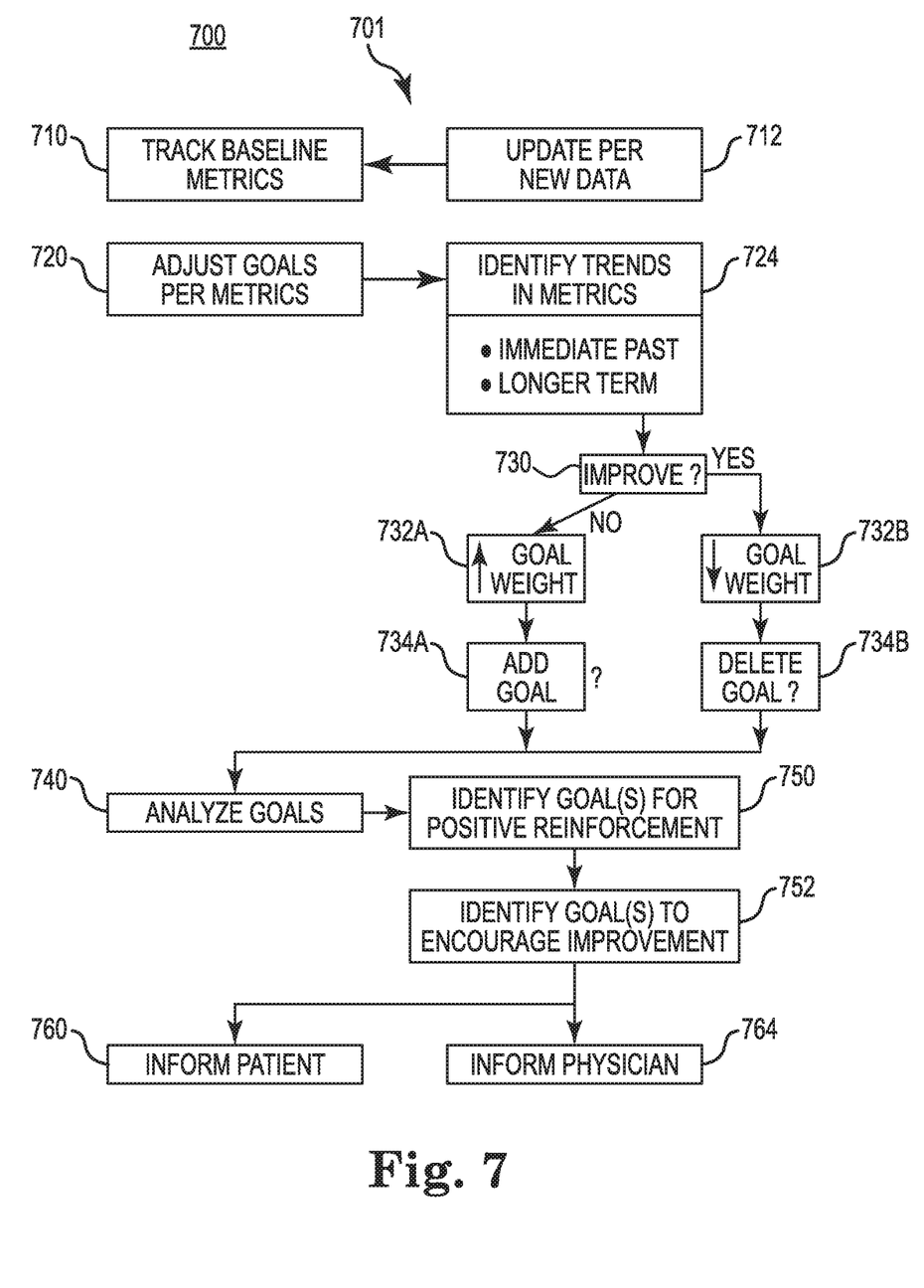
FIG. 7 is a flow diagram of a patient management protocol, according to one example of the present disclosure.

FIG. 7 is a flow diagram schematically illustrating a therapy management protocol 701, according to one example of the present disclosure. In some examples, protocol 701 operates as part of a therapy manager 550, 562 within the patient management system of FIG. 6A. As shown in FIG. 7, protocol 701 includes a general function of tracking baseline metrics (at 710), which includes maintaining over time a history of patient therapy metrics to provide a baseline from which to evaluate and adjust current therapy. As shown at 712, the baseline metrics are maintained via periodic updates of new data.

Protocol 701 further includes adjusting therapy goals per therapy metrics, as shown at 720. In one aspect, this adjustment includes identifying trends in the therapy metrics, as at 724. In some examples, the trend identification is performed for immediate past behavior, such as in the last week or last day. In some examples, the trend identification is performed according to longer term behavior, such as the last month, last three months, etc. In identifying and evaluating trends, the protocol queries at 730 whether an improvement has occurred due to the therapy. If the answer is YES, then the protocol 701 implements a change, such as decreasing a weighted value for a goal (at 732B) or deleting a goal (at 734B). On the other hand, if the answer is NO, then the protocol 701 implements a change, such as increasing a weighted value of a goal (at 732A) or adding a goal (at 734A). Such goals might include, but are not limited to, a number of nights/week that therapy was used, an "on" duration for any given night, a decrease in AHI, an increase in therapy intensity, qualitative rating re day time alertness, etc.

Once the protocol completes these queries and adjustments in view of multiple goals and trends, at 740 the protocol 701 includes analyzing the adjusted goals. In some examples, such analysis includes identifying goal(s) for which the patient should receive positive reinforcement, as at 750. In some examples, such analysis includes identifying goal(s) for which the patient should receive encouragement to make improvements, as at 752.

Once this analysis is complete, using pre-established messaging available via goals function 552 of therapy manager 550 (or other therapy manager), the protocol 701 includes informing the patient (760) and/or the physician (764) of the goals along with the respective positive reinforcement and/or encouragement for improvement. In some examples, such communications include recommendations and/or tools on how best to achieve such goals.

In this way, the patient management system will serve to integrate therapy metrics collected from the patient programmer, patient experience and physician or care giver feedback for overall sleep health management. In some examples, a master therapy manager of the patient management system performs automated analysis of therapy metrics to provide patients with relevant feedback via their patient user interface and with some actionable parameters being prepared for transmission into the patient control to guide therapy.

Although specific examples have been illustrated and described herein, it will be appreciated by those of ordinary skill in the art that a variety of alternate and/or equivalent implementations may be substituted for the specific examples shown and described without departing from the scope of the present disclosure. This application is intended to cover any adaptations or variations of the specific examples discussed herein.

What is claimed is:

1. A patient remote control for an implantable medical device to deliver an electrical stimulation therapy, comprising:
   a housing containing circuitry inlcuding an element to at least wirelessly communicate with the implantable medical device and including a top surface;
   a first electronic input comprising a finger-activatable first button in communication with the circuitry to cause a communicatio to the implantable medical device when the first button is activated to turn on or pause the electrical stimulation therpy, wherein the first button defines at least a first recess and is accesible at the top surface of the housing, wherein the first button comprises a first size and a first shape;

a second electronic input comprising a finger-activatable second button in communication with the circuitry to cause a communication to the implantable medical device when the second button is activated to turn off the electrical stimulation therapy, wherein the second button is located within a first recess and second recess formed at and within the top surface of the housing, the second button comprising a second size substantially less than the first size of the first button and the second button comprising a second shape different than the first shape of the first button; and a third electronic input comprising at least one finger-activatable third button in communication with the circuitry to cause a communication to the implantable medical device when the at least one third button is activated to provide at least one of an increase and a decrease in an intensity of the electrical stimulation therapy delivered by the implantable medical device, wherein the at least one third button is raised relative to the top surface and interposed between the first input and the second input, and wherein the at least one third button comprises a third size different than the first and second sizes, and the third button comprises a third shape different than the first and second shapes.

2. The patient remote control of claim 1, and further comprising the implantable medical device, which comprises an implantable pulse generator for treating obstructive sleep apnea via the electrical stimulation therapy.

3. The patient remote control of claim 1, wherein the housing comprises a generally flat bottom surface and the top surface is sloped from a first end having a first elevation to a second end having a second elevation greater than the first elevation, with the first input being adjacent the first end and the second input being closer to the second end than the first input.

4. The patient remote control of claim 1, wherein the second input is spaced apart from the third input by a first distance and the first input is spaced apart from the third input by a second distance, wherein the first distance is substantially greater than the second distance.

5. The patient remote control of claim 1, wherein the first input and the third input are generally centered along a central longitudinal axis of the housing extending between a first end and a second end of the housing, and the second input is aligned parallel to but spaced laterally apart from the central longitudinal axis.

6. The patient remote control of claim 1, wherein the at least one third button of the third input comprises two third buttons spaced apart from each other and one of the two third buttons provides the increase in the intensity of the electrical stimulation therapy and the respective third button provides the decrease in the intensity of the electrical stimulation therapy.

7. The patient remote control of claim 1, further comprising:
a first display element at least partially surrounding the first button of the first input, wherein the first display element provides illumination in a first color to represent an on state of the implantable medical device and in a second color to represent an off state of the implantable medical device.

8. The patient remote control of claim 1, wherein the housing includes a bottom surface opposite the top surface, and further comprising:
a display on the bottom surface and including a linear array of visual indicators indicative of a relative stimulation strength setting for the electrical stimulation therapy in which an increased number of active visual indicators of the display corresponds to a relatively higher intensity of the electrical stimulation therapy as set by finger-activation of the at least one third button of the third input and a decreased number of active visual indicators of the display corresponds to a relatively lower intensity of the electrical stimulation therapy as set by a finger-activation of the at least one third button of the third input 3.

9. The patient remote control of claim 1, wherein the first shape of the first button of the first input is generally rectangular, and the first size of the first button of the first input comprises a first area larger than an area of an average patient's thumb print, and the second size of the second button of the second input comprises a second area generally equal to or less than the area of the average patient's thumb print.

10. The patient remote control of claim 1, wherein the first recess of the first button of the first input comprises a depth substantially greater than a depth of the second recess of the second input in which the second button is located.

11. The patient remote control of claim 1, wherein the on function of the first input, upon a pressing of the finger-activatable first button, is to cause at least one of an initiation of the electrical stimulation therapy and a pause of the electrical stimulation therapy, and wherein the off function of the second input, upon a pressing of the finger-activatable second button, is to cause termination of the electrical stimulation therapy.

12. The patient remote control of claim 1, and further comprising:
a control portion, in cooperation with the circuitry, is to receive a confirmation communication from the implantable medical device when a wireless communication from the patient remote control cause by a respective one of the first, second, and third inputs is accepted by the implantable medical device,
wherein the control portion is to cause, via the circuitry, periodically repeat sending the wireless communication until the confirmation is received from the implantable medical device, and upon such receipt of the confirmation, to produce a notification regarding receipt of the confirmation.

13. The patient remote control of claim 12, wherein the notification is communicated according to a type including at least one of a success indication function, a failure indication function, and a limit indication function.

14. The patient remote control of claim 12, wherein the notification is communicated according to a mode including at least one of an audible indication function, a visual indication function, and a vibration indication function.

15. The patient remote control of claim 12, wherein the control portion is to cause operation of the wireless communication according to a low power, short range wireless communication protocol and to cause the repeated sending of the wireless communication, initiated by a finger-activation of a respective one of the first, second, and third inputs for a frequency and number of iterations sufficient to enable positioning of the patient remote control, relative to a body in which the implantable medical device is implanted, after the wireless communication per a repsective one of the first, second, and third inputs is initiated.

16. A patient remote control for an implantable pulse generator, comprising:

a housing containing circuitry and including a top surface, wherein the circuitry comprises a wireless element to wireless communicate with the implantable pulse generator;

a first electronic input comprising a finger-activatable first button in communication with the circuitry to cause a communication to the implantable pulse generator when the first button is activated to initiate or pause the electrical stimulation therapy, wherein the first button defines at least a first recess relative to the top surface, with the first button comprising a first size and a first shape, and wherein the first recess comprises a first depth; and a second electronic input comprising a finger-activatable second button in communication with the circuitry to casue a communication to the implantable pulse generator when the second button is activated to terminate the electrical stimulation therapy, wherein the second button is located within a second recess formed at and within the top surface, wherein the second button comprises a second size substantially less than the first shape of the first button, and the second button comprises a second shape different than the first shape of the first button, and wherein the second recess of the second input comprises a second depth sunstantially less than the first depth of the first recess of the first button; and a third electronic input comprising at least one finger-activatable third button in communication with the circuitry to cause a communication to the implantable pulse generator when the at least one third button is activated to cause at least one of an increase and a decrease in an intensity of the electrical stimulation therapy delivered by the implantable pulse generator, wherein the at least one third button is raised relative to the top surface and interposed between the first input and the second input, with the at least one third button comprising a third size different than the first and second sizes of the respective first and second buttons, and the at least one third button comprising a third shape different from the first and second shapes of the respective first and second buttons, wherein the at least one third button of the third input comprises two third buttons spaced apart from each other and arranged to at least partially surround the first button of the first input, and wherein upon finger activation, one of the two third buttons is to cause the increase in the intensity of the electrical stimulation therapy and the other respective third button is to cause the decrease in the intensity of the electrical stimulation therapy.

17. The patient remote control of claim 16, wherein the first shape of the first button of the first input is generally rectangular, and the first size of the first button of the first input comprises a first area larger than an area of an average patient's thumb print, and the second size of the second button of the second input comprises a second area generally equal to or less than the area of the average patient's thumb print.

* * * * *

UNITED STATES PATENT AND TRADEMARK OFFICE
CERTIFICATE OF CORRECTION

PATENT NO. : 11,324,953 B2
APPLICATION NO. : 16/670731
DATED : May 10, 2022
INVENTOR(S) : Rondoni et al.

It is certified that error appears in the above-identified patent and that said Letters Patent is hereby corrected as shown below:

In the Claims

Column 18, Line 57, Claim 1, delete "inlcuding" and insert in place thereof --including--.

Column 18, Line 62, Claim 1, delete "communicatio" and insert in place thereof --communication--.

Column 18, Line 65, Claim 1, delete "accesible" and insert in place thereof --accessible--.

Column 19, Line 6, Claim 1, delete "first recess and".

Column 19, Line 51, Claim 6, delete "the respective" and insert in place thereof --the other respective--.

Column 20, Line 8, Claim 8, delete "a".

Column 20, Line 9, Claim 8, delete "3".

Column 20, Line 35, Claim 12, delete "cause" and insert in place thereof --caused--.

Column 20, Line 61, Claim 15, delete "repsective" and insert in place thereof --respective--.

Column 21, Line 16, Claim 16, delete "casue" and insert in place thereof --caused--.

Column 21, Line 22, Claim 16, delete "shape" and insert in place thereof --size--.

Column 21, Line 25, Claim 16, delete "sunstantially" and insert in place thereof --substantially--.

Signed and Sealed this
Sixteenth Day of August, 2022

*Katherine Kelly Vidal*
Katherine Kelly Vidal
*Director of the United States Patent and Trademark Office*